United States Patent [19]

Sohn et al.

[11] Patent Number: 4,484,919
[45] Date of Patent: Nov. 27, 1984

[54] RECTAL AREA DRESSING

[75] Inventors: Norman Sohn, Englewood, N.J.; Michael A. Weinstein, Scarsdale; Richard D. Robbins, New York, both of N.Y.

[73] Assignee: Affiliated Surgical Supplies, Englewood, N.J.

[21] Appl. No.: 436,192

[22] Filed: Oct. 25, 1982

[51] Int. Cl.³ .......................................... A61F 13/16
[52] U.S. Cl. .................................................... 604/358
[58] Field of Search ................ 604/358, 364, 359, 377, 604/385

[56] References Cited

U.S. PATENT DOCUMENTS

| | | | |
|---|---|---|---|
| Re. 24,385 | 10/1957 | Flanders | 604/358 |
| 3,570,489 | 3/1971 | Brown | 604/358 X |
| 3,906,952 | 9/1975 | Zamist | 604/358 |
| 4,010,754 | 3/1977 | Pieniak | 604/389 |
| 4,072,151 | 2/1978 | Levine | 604/358 |
| 4,182,335 | 1/1980 | Matrullo | 604/358 X |

Primary Examiner—Yasko
Attorney, Agent, or Firm—Gottlieb, Rackman & Reisman

[57] ABSTRACT

There is disclosed a rectal area dressing for controlling discharge from the rectoperineal body portion for use by incontinent persons having anal musculature complications. The rectal area dressing includes an elongated absorbent pad configured for conforming arrangement within the lowermost portion of the rectum and natal cleft for absorbtion of rectal discharge. A non-permeable adhesive material is affixed to the base exterior surface of the elongated absorbent pad to maintain the exterior of the rectal dressing free from rectal discharge. The rectal area dressing also includes a pressure-sensitive adhesive tape to secure the elongated absorbent pad within the natal cleft. The adhesive tape includes a central section which is affixed to the base of the elongated pad and extending end members which adhere to the skin surfaces in the rectoperineal body portion.

19 Claims, 7 Drawing Figures

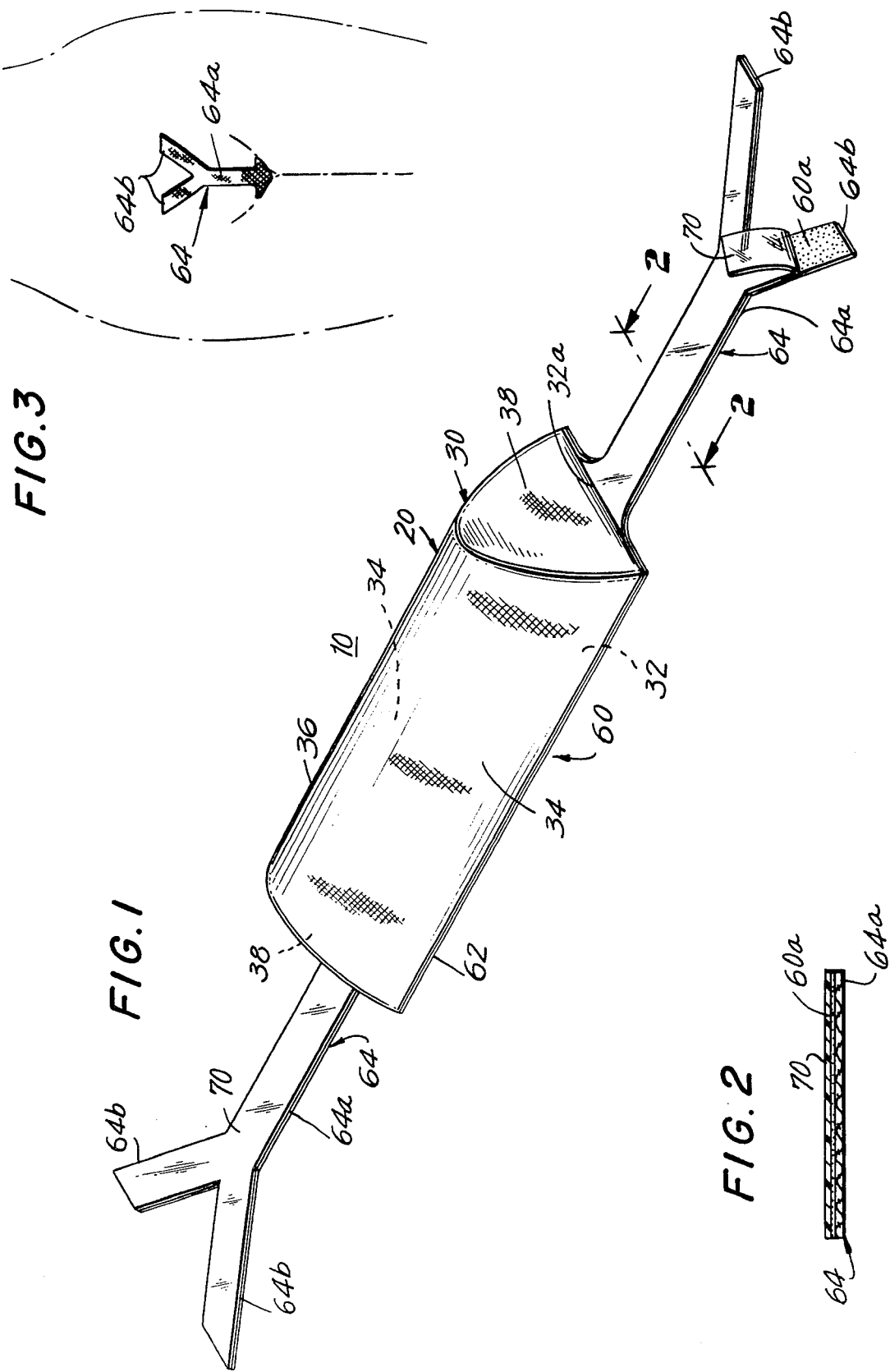

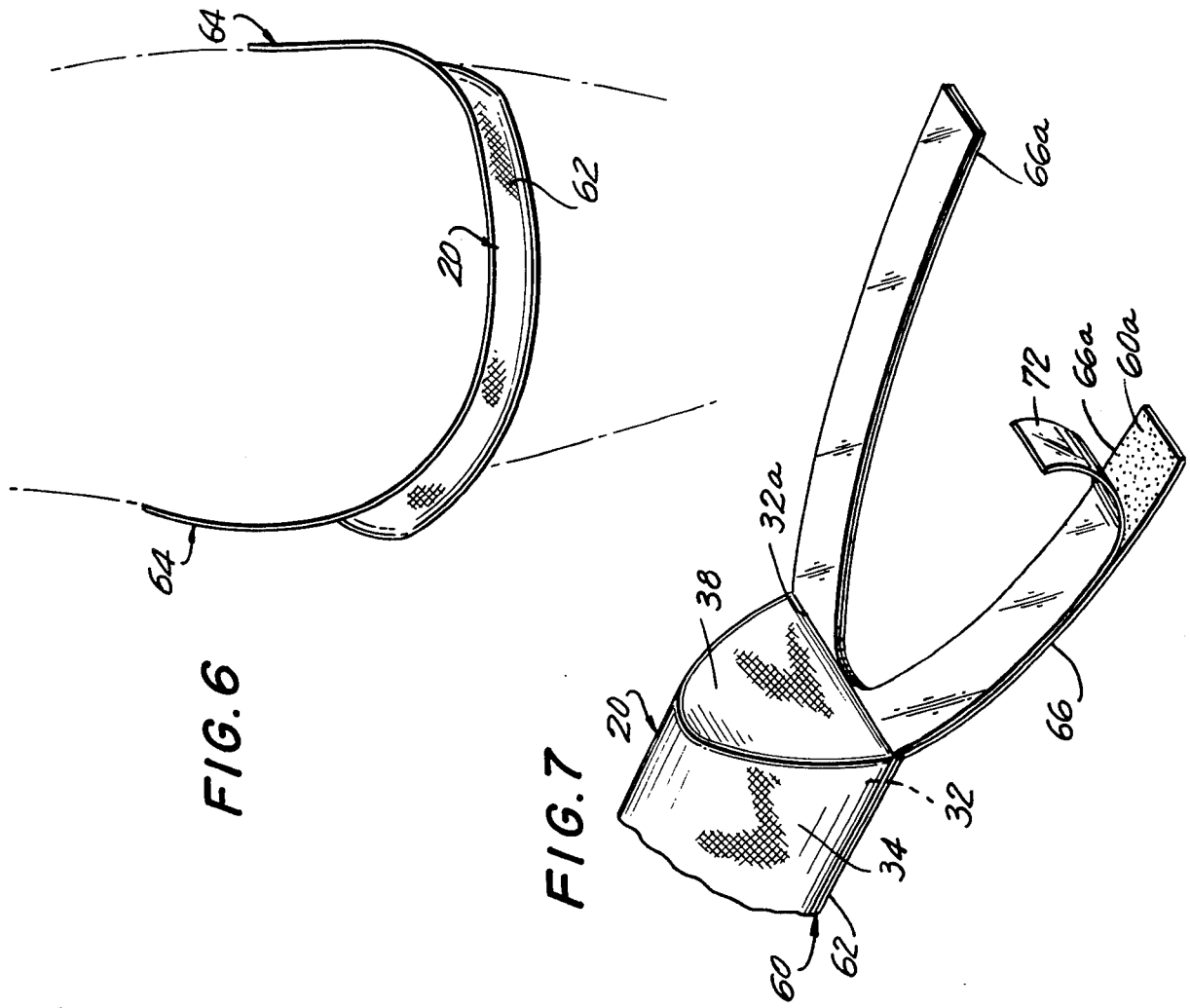

RECTAL AREA DRESSING

TECHNICAL FIELD

The present invention relates to a rectal area dressing for controlling discharge from the rectoperineal body portion for use by incontinent persons having anal musculature complications. More particularly, the invention is concerned with a rectal area dressing which will absorb the discharge of bodily fecal excretions, including improved design features which permit optimal coaptative arrangement of the dressing on the perineum portion of the body. The rectal area dressing, by its design, conforms to the anatomy of the natal cleft where it is secured in position to permit its usage during all phases of a person's normal physical activity.

BACKGROUND ART

Therapeutic dressings and medicated pads which will absorb the discharge of bodily fluids are generally well-known in the medical arts and in the medical industry. In the rectal perineal area, such dressings are required for use by persons affected by minor uncontrollable discharge of fecal products associated with pathological conditions of the colon and rectum. By way of example, patients who have had rectal or colon surgery often have some degree of incontinence associated with deterioration of the rectal sphincter muscles. Paraplegic and quadriplegic persons also often have an associated paralysis of the sphincter muscles requiring rectal dressings for use following prophylactic enema procedures. For these purposes, the medical arts field has recognized the need to provide disposable rectal area dressings for the control of inadvertent discharge of bodily fluids in the rectal perineal portion of the body. But these dressings have often proved to be inadequate in many cases.

Heretofore, it has been common to employ rectal napkins fabricated out of cellulose fibers or cotton for use in the control of inadvertent rectal discharge. In such known napkin arrangements, layers of cloth and absorbent cellulose fiber or cotton materials are commonly formed into pads of planar configuration which are positioned in the natal cleft in the rectal area adjacent the anus. A disposable napkin arrangement of this type is exemplified by the teachings of U.S. Pat. No. Re. 24,385 to Flanders. This patent discloses a napkin arrangement formed of a pad of uniform thickness including exterior cloth facing members which enclose an absorbent material. The pad is adapted for insertion edgewise into the "human anal declivity" opposing the anus where it is held in position by a "gripping action" of the skin surfaces in the declivity. To this end, the pad is provided with an interior edge surface, which conforms to the curvature of the innermost portion of the anal declivity, and an exterior edge portion, which conforms to the curvature of the outermost points of contact of the skin forming the anal declivity. The Flanders patent asserts that this arrangement attains a maximal coaptative engagement of the napkin and the skin surfaces in the crotch region of the body to effect a secure placement of the napkin.

In general, anal napkins such as are exemplified by Flanders have not proven entirely satisfactory in practice. It will be appreciated, for example, that the exterior surfaces of such napkins abrasively contact the skin surfaces of the natal cleft when the person using the napkin is ambulatory. This has a tendency to irritate the skin of the rectal perineal body portion, causing chafing and related skin disorders. Furthermore, any movement of the napkin from the precise position adjacent the anus, which may be occasioned by activity of the person using the napkin, limits the effectiveness of the napkin in preventing inadvertent fecal discharge.

Another prior art arrangement is shown in U.S. Pat. No. 4,182,335 to Matrullo. This patent discloses an anal filter fabricated of flexible materials which may be conformingly arranged adjacent the anus for absorption of rectal discharge. The anal filter includes a base layer made of porous flexible material and an absorbent rectal facing layer of "fluffy" non-woven fibrous material. The anal filter is positioned in overlying relation with respect to the anus by "non-adhesive" adherence of the fibrous material layer. Although the Matrullo arrangement operates satisfactorily in theory, practical difficulties are presented associated with chafing and irritation as in prior art napkin arrangements by reason of the mechanical adherence of the "fluffy" non-woven fibrous layer of the filter. Further difficulties are presented in positioning the filter in secure relation to the anus in order to prevent inadvertent rectal discharge.

An alternative approach of the prior art is exemplified by U.S. Pat. No. 3,570,489 to Brown, where there is disclosed a device for insertion into the anus to block undesirable rectal discharge. Brown's device comprises a stiff but relatively slender stem which is provided with an intrarectal anchoring member of a conical configuration at one end and a mass of fibrous absorbent material at an opposing terminal end. The conical anchoring member of the device is inserted through the anus into the rectum in order to position the fibrous material adjacent the anus for absorption of rectal discharge. In general, rectal insertion devices in accordance with the teachings of Brown, have not proven satisfactory as they require that a patient have properly developed anal sphincter muscles to secure the device in proper position adjacent the anus. Where the spincter muscles are paralyzed, malformed or otherwise impaired, such devices are ineffective. Moreover, in order for such devices to function properly, they must be securely positioned against movement relative to the anus, which is difficult to attain where a patient is active and mobile. In addition, activities of a person using the device will also occasion irritation in the anal canal of the rectum by reason of movement of the device.

Insofar as applicants are aware, other teachings of the art are primarily directed to dressings for the absorption of a woman's menstrual discharge and as such do not address the physiological requirements for rectal area dressings. Such vaginal area dressings are represented by U.S. Pat. Nos. 4,072,151 to Levine and 3,906,952 to Zamist.

Accordingly, it is a broad object of the present invention to provide an improved rectal area dressing.

A more specific object of the present invention is to provide a rectal area dressing including improved design features which attain coaptative non-abrasive arrangement of the dressing on the perineum portion of the body.

Another object of the present invention is to provide a rectal area dressing having improved design features which facilitate positioning of the dressing in conforming relation on the perineum portion of the body which may be secured in position without interference with a person's normal physical activity.

A still further object of the present invention is to provide a rectal area dressing having improved manufacturing advantages to permit inexpensive fabrication of a dressing which is readily disposable.

DISCLOSURE OF THE INVENTION

In the present invention, these purposes, as well as others which will be apparent, are achieved generally by providing a rectal area dressing in the form of an elongated absorbent pad having a substantially triangular cross-section, including a generally planar base surface and contiguous planar side surfaces which conform to the contour of the natal cleft. The elongated absorbent pad includes an exterior cover fabricated of a permeable and absorbent fabric, an absorbent filler material encased within the cover and a pressure sensitive adhesive tape which may be secured to the base of the pad for positioning the planar side surfaces of the pad in conforming coaptative relation with the skin surfaces of the natal cleft in the perineum portion of the body. The adhesive tape may be provided with end members extending exteriorly of the elongated pad adapted for non-irritating adhesion to the skin surfaces in the rectal perineal area. The elongated absorbent pad also includes a non-permeable adhesive backing material which may be laminated to the adhesive tape for purposes of preventing passage of rectal fluids through the exterior cover of the rectal dressing. According to a preferred embodiment of the invention, the exterior cover is fabricated of a non-woven latex-bonded pulp and the absorbent filler material is a cellulose loosely packed fiber. In this embodiment, the pressure sensitive adhesive tape is fabricated of a non-permeable flexible poly-olefinic base and the non-permeable laminated backing member is a hypoallergenic knitted tape.

Other objects, aspects, features and advantages of the present invention will be apparent when the detailed description of the preferred embodiment of the invention is considered in conjunction with the drawings which should be construed in an illustrative and not limiting sense, as follows:

BRIEF DESCRIPTION OF DRAWINGS

FIG. 1 shows an overall perspective view of the dressing, including an elongated absorbent pad, non-permeable backing member, and adhesive fastening tape;

FIG. 2 is a cross-sectional view taken along the line 2—2 of FIG. 1, illustrating the component layers of the adhesive tape including a peel-away non-adhesive protective cover;

FIG. 3 is a frontal body view of a female patient illustrating the manner in which the rectal dressing is fastened within the natal cleft;

FIG. 4 illustrates the appearance of the dressing of FIG. 3 viewed from the rear of the patient;

FIG. 5 is a cross-sectional view through the elongated pad, taken along the plane defined by arrows 5—5 of FIG. 4;

FIG. 6 is a side view of the dressing attached to a patient indicating its appearance in the crotch area; and FIG. 7 is a fragmentary perspective view of an alternate embodiment of the fastening arrangement for the rectal dressing, showing a "wishbone" approach for use by male patients.

BEST MODE FOR CARRYING OUT INVENTION

Referring now to the drawings and, more particularly, to FIGS. 1 through 5 thereof, there is illustrated a rectal area dressing according to the present invention, generally designated 10, consisting of an elongated absorbent pad 20 configured to conform to the contour of the natal cleft, and a fastening means for positioning the absorbent pad 20 in conforming relation within the lowermost portion of the rectum and natal cleft for absorption of rectal discharge.

The absorbent elongated pad 20 has a permeable esterior cover 30 having a substantially triangular cross-section defined by a generally planar base surface 32, contiguous inwardly disposed side surfaces 34 extending from the base surface 32 and terminating in a longitudinally extending apical surface 36 and inwardly disposed end surfaces 38. The exterior cover 30 is preferably formed of a non-woven latex-bonded wood or pulp which illustratively may have a water-holding capacity in the range of 10 to 25 grams per gram of substrate of material. By way of example, the exterior cover 30 may be a non-woven latex wood pulp fabric commercially available under the trademark "Airtex", manufactured by The James River Paper Company, Richmond, Va. "Airtex" dressing product designations SC 130 HB and SC 150 HB which have water holding capacities of 22 and 15 grams per gram of substrate of material, respectively, have superior absorption characteristics for employment in the fabrication of the rectal area dressing 10 of the present invention.

An absorbent filler material 40, preferably fabricated of a cellulose material, is encased within the exterior cover 30. The absorbent filler material 40 retains rectal discharge which permeates through exterior cover 30. In order to provide maximal comfort to the wearer of the rectal dressing 10, the absorbent filler material 40 should have excellent absorbency and bulk in order that rectal discharge fluids permeate fully through the exterior cover and maintain the exterior skin-contacting surfaces of the elongated absorbent pad 20 relatively dry and free from discharge products. To this end, the absorbent filler 40 is loosely compacted within the exterior cover 30 of the elongated absorbent pad 20 in order to allow for uniform absorbency within the entire longitudinal length and cross section of the elongated absorbent pad 20.

In the preferred embodiment of the invention, the absorbent filler material 40 is formed of a cellulose wood fiber marketed under the trademark "Supersoft" and available from International Pulp Sales Company of New York, N.Y. Its characteristics are as follows:

| "Supersoft" Cellulose Pulp | |
|---|---|
| Fiber | Southern Pine |
| Brightness | 86 General Electric Standard |
| Apparent Density | 0.50–0.57 g/cc |
| Basis Weight | 139 lbs. per 1000 sq. ft. |
| Moisture | 6.0 plus or minus 2 percent |

As presently marketed, "Supersoft" cellulose fiber is available in material mesh gradations ranging from 14 to to excess 100 having Clark fiber classification percentages ranging from 45% to 10.5% respectively. "Supersoft" cellulose pulp having a 14 mesh gradient with corresponding Clark fiber classification of 42% has been found to be optimal for employment in the rectal area dressing 10 of this invention.

The base surface 32 of the exterior cover 30 may be provided, on its exterior surface, with a non-permeable adhesive layer of material 50, such as a flexible polyolefinic base adhesive tape, or the like, which is affixed to the entire longitudinal and cross-sectional surface of the exterior base surface 32 of the elongated absorbent pad 20 (see FIG. 5). The non-permeable adhesive 50 provides reserve protection for the user of the rectal area dressing 10 by maintaining the exteriorly exposed base surface 32 clean and free of fecal discharge. A pressure-sensitive adhesive tape which is effective as a non-permeable backing member is available commercially under the trademark "Dermiclear" which is marketed by Johnson & Johnson Products, Inc. of New Brunswick, N.J. "Dermiclear" is a flexible transparent adhesive tape fabricated of a poly-olefinic base material.

The elongated absorbent pad 20 is secured in conforming relation within the natal cleft by a fastening means including a pressure-sensitive tape 60 which overlies the non-permeable layer of material 50 and the base surface 32 of the exterior cover 30, and adhesively contacts the skin surfaces in the rectoperineal body area. The non-permeable adhesive layer of material 50 is preferably laminated to the pressure-sensitive tape 60 to provide an integral backing for the rectal dressing 10.

Alternative embodiments of the rectal area dressing 10 are illustrated in FIGS. 1-6 and 7.

In the embodiment shown in FIGS. 1-6 the pressure sensitive tape 60 is provided with a configuration having particular application for the anatomy of female patients. The pressure-sensitive tape 60 of this embodiment includes a central section 62 which overlies base surface 32 of the exterior cover surface 30, and end members 64 which extend exteriorly of the transverse edges 32a of the base cover surface 32. The exteriorly extending end members 64 have "Y" shaped configurations, including longitudinally extending sections 64a and contiguous angularly opposed terminal end sections 64b. The adhesive tape 60 is provided with an adhering surface 60a, as shown in FIG. 2, and peel-off non-adhesive protective coverings 70 which overlie the exteriorly extending end-members 64 of the adhesive tape 60. The coverings 70 facilitate handling of the rectal area dressing 10 prior to use and also prevent the adhering surface 60a from drying out or otherwise deteriorating.

An alternative embodiment of the invention, illustrated in FIG. 7, incorporates a pressure-sensitive tape 60 design which accommodates the male anatomy. The adhesive tape 60 of this embodiment is provided with an exteriorly extending end member 64 having a "Y" shaped configuration, as described above and an end member 66 having a "wishbone" configuration. The exteriorly extending end member 66 has generally opposing sections 66a which extend contiguously from the central adhesive section 62 at the transverse edge 32a of the base cover surface 32. As in the first described embodiment of the invention, adhesive tape 60 is provided with adhering surfaces 60a. The end member 66 also includes peel-off non-adhesive protective coatings 72 which overlie the exteriorly extending opposing sections 66a.

In application of the rectal area dressing 10, the elongated absorbent pad 20 is positioned in conforming relation within the natal cleft as shown in FIGS. 3-5. The non-adhesive coverings 70, 72 are then removed to permit adhesive attachment of the exteriorly extending end members 64, 66 to the skin surfaces in the rectal perineal area.

Adhesive tape 60 is preferably fabricated of a hypoallergenic knitted tape which adheres securely to the skin with minimal skin irritation. Such an adhesive tape is commercially available under trademark "Dermiform" which is manufactured by Johnson & Johnson Products, Inc., New Brunswick, N.J. "Dermiform" hypoallergenic knitted tape has adhesive characteristics which are non-irritating to the skin and which maintain the rectal area dressing 10 of the present invention in secure relation within the natal cleft of the perineal body portion during a person's normal physical activity.

From the foregoing, it will be appreciated that the present invention provides a rectal area dressing 10 which overcomes difficulties of prior art arrangements and which achieves the objects stated heretofore.

In particular, the present invention provides a rectal area dressing 10 including improved design features which permit its secure arrangement within the perineum portion of the body for all phases of a person's normal physical activity. The rectal area dressing 10 is advantageously provided in the form of an elongated absorbent pad 20 configured to conform to the contour of the natal cleft for non-irritating arrangement therein.

More particularly, the elongated pad 20 includes an exterior cover 30, formed of an absorbent non-woven latex wood pulp fabric and an interior absorbent cellulose filler material 40 for containing rectal discharge. On the base surface 32 of the exterior 30 there is provided a non-permeable flexible poly-olefinic base adhesive tape 50 which maintains the exterior base surface 32 of the exterior cover 30 free from rectal discharge for maximal comfort to the wearer of the dressing. A secure non-irritating adhesion of the elongated pad 20 to the skin surfaces in the rectal perineal area is provided by a pressure-sensitive adhesive tape 60 which is secured to the base surface 32 of the exterior cover 30. The pressure sensitive adhesive tape 60, in alternative embodiments of the invention, is provided with extending end members having "Y" and "wishbone" configurations 64, 66 adapted for secure arrangement to skin surfaces in the rectal perineal area of both male and female patients.

Numerous modifications are possible in light of the disclosure. By way of example, there is a disclosed arrangement of the non-permeable backing 50 fabricated of a flexible poly-olefinic base adhesive tape and a pressure-sensitive adhesive tape 60 fabricated of a hypoallergenic knitted tape which adheres to the skin with minimal skin irritation. Those skilled in the art will appreciate that other materials may be employed to fabricate non-permeable backing 50 and pressure sensitive tape 60. For example, the arrangement of "Dermaclear" non-permeable backing 50 and "Dermaform" hypoallergenic knitted fastening tape 60 may be replaced with a polypropylene stretchable fabric for purposes of providing an adhesive non-permeable backing for exterior base surface 32. However, it should be noted that polypropylene stretchable fabrics do not have the adhesive characteristics of "Dermaform" hypoallergenic knitted tape. Accordingly, when such polypropylene backings are employed, it is preferable to also employ a non-irritant pressure sensitive adhesive to the rectal area dressing base surface 32 in order to provide reserve adhesive capacity for the rectal area dressing 10.

Similarly, although there has been disclosed a pressure sensitive adhesive tape 60 having "Y" and "wishbone" configurations 64, 66 for securing the elongated pads 20 within the natal cleft, other end member configurations may be devised. In this regard, it will be appreciated that the dimensions and configurations of the presure sensitive adhesive tape 60 may be varied to provide adhesive characteristics which accommodate different levels of physical activity of persons using the rectal area dressing 10.

It is to be understood, therefore, that the above-described embodiments are merely illustrative and other embodiments may be devised by those skilled in the art, without departing from the spirit or scope of the present invention, as set forth in the appended claims.

We claim:

1. A rectal area dressing for controlling discharge from the rectoperineal body portion, said rectal dressing being adapted for positioning within the natal cleft in the perineum portion of a person's body, said rectal dressing comprising:
   (a) an elongated absorbent pad configured to conform to the contour of the natal cleft for close fitting relation therewith, said elongated absorbent pad having a substantially triangular cross-section, including a generally planar base surface, contiguous planar side surfaces, and a longitudinally extending apical surface, said planar side and apical surfaces being adapted for resilient and conforming positioning within the natal cleft, said base surface extending exteriorly of said natal cleft;
   (b) non-permeable backing means integral with the base surface of said absorbent pad for retaining rectoperineal discharge within said absorbent pad; and
   (c) means for fastening said absorbent pad within the natal cleft in sealing and conforming relation therewith.

2. A rectal area dressing according to claim 1, wherein said elongated absorbent pad includes an exterior cover fabricated of a permeable and absorbent fabric, and an absorbent filler material encased within said exterior cover.

3. A rectal area dressing according to claim 2, wherein said non-permeable backing means includes a non-permeable adhesive material affixed to the base surface of said elongated absorbent pad.

4. A rectal area dressing according to claim 3, wherein said pad fastening means includes a pressure-sensitive adhesive tape integral with said backing material, said adhesive tape including end members extending exteriorly of said elongated pad adapted for non-irritating adhesion to skin surfaces in the rectoperineal area.

5. A rectal dressing according to claim 4, wherein said adhesive tape is fabricated of a hypoallergenic knitted tape.

6. A rectal dressing according to claim 5, wherein said non-permeable backing material is laminated to said hypoallergenic knitted tape.

7. A rectal area dressing according to claim 4, wherein the end members of said adhesive tape have "Y" shaped configurations, including sections extending longitudinally from said elongated pad, and angularly opposed sections extending therefrom.

8. A rectal area dressing according to claim 7, wherein said "Y" shaped end members include non-adhesive protective coverings to facilitate handling of the rectal dressing prior to use.

9. A rectal area dressing according to claim 4, wherein at least one of said end members has a "wishbone" configuration, including outwardly extending opposing sections, and non-adhesive protective coverings.

10. A rectal area dressing for controlling discharge from the rectoperineal body portion, said rectal dressing being adapted for positioning within the natal cleft in the perineum portion of a person's body, said rectal dressing comprising:
    (a) an elongated absorbent pad configured to conform to the contour of the natal cleft for close fitting relation therewith, said elongated pad including an exterior cover fabricated of a permeable and absorbent fabric, and an absorbent filler material encased within said exterior cover, said exterior cover having a substantially triangular cross-section, including a generally planar base surface, and contiguous planar side surfaces terminating in a longitudinally extending apical surface, said planar side surfaces and said absorbent filler material coacting for resilient positioning of the rectal dressing within the natal cleft;
    (b) non-permeable backing means integral with the base surface of said absorbent pad for retaining rectoperineal discharge within said absorbent pad; and
    (c) means for fastening said absorbent pad within the natal cleft in sealing and conforming relation therewith.

11. A rectal area dressing according to claim 10, wherein said non-permeable backing means includes a non-permeable adhesive material affixed to the base surface of said elongated absorbent pad.

12. A rectal area dressing according to claim 11, wherein said exterior cover is fabricated on a non-woven latex bonded pulp.

13. A rectal area dressing according to claim 12, wherein said absorbent filler material is a cellulose fiber.

14. A rectal area dressing according to claim 13, wherein said non-permeable adhesive material is fabricated of a flexible poly-olefinic base.

15. A rectal area dressing according to claim 14, wherein said pad fastening means includes a pressure sensitive adhesive tape integral with said flexible poly-olefinic base material, said adhesive tape including end members extending exteriorly of said elongated pad adapted for non-irritating adhesion to skin surfaces in the rectoperineal area.

16. A rectal dressing according to claim 15, wherein said adhesive tape is fabricated of a hypoallergenic knitted tape.

17. A rectal dressing according to claim 16, wherein said flexible poly-olefinic base material is laminated to said hypoallergenic knitted tape.

18. A rectal area dressing according to claim 17, wherein the end members of said adhesive tape have "Y" shaped configurations, including sections extending longitudinally from said elongated pad, and angularly opposed sections extending therefrom.

19. A rectal area dressing according to claim 18, wherein said "Y" shaped end members include non-adhesive protective coverings to facilitate handling of the rectal dressing prior to use.

* * * * *